(12) United States Patent
Mohmmadizand

(10) Patent No.: US 9,395,285 B2
(45) Date of Patent: Jul. 19, 2016

(54) TISSUE PROCESSING AND SLIDE STAINING APPARATUS WITH ROBOTIC ARM HAVING THREE DEGREES OF FREEDOM

(71) Applicant: Ramin Mohmmadizand, Karaj (IR)

(72) Inventor: Ramin Mohmmadizand, Karaj (IR)

( * ) Notice: Subject to any disclaimer, the term of this patent is extended or adjusted under 35 U.S.C. 154(b) by 0 days.

(21) Appl. No.: 14/969,975

(22) Filed: Dec. 15, 2015

(65) Prior Publication Data

US 2016/0097701 A1    Apr. 7, 2016

(51) Int. Cl.
*G01N 31/16* (2006.01)
*G01N 1/31* (2006.01)
*G01N 35/00* (2006.01)

(52) U.S. Cl.
CPC .......... *G01N 1/312* (2013.01); *G01N 35/00029* (2013.01); *G01N 35/0099* (2013.01); *G01N 35/00623* (2013.01); *G01N 35/00871* (2013.01); *G01N 2035/00138* (2013.01); *G01N 2035/00168* (2013.01); *G01N 2035/00346* (2013.01); *Y10S 901/02* (2013.01)

(58) Field of Classification Search
CPC ............................... G01N 1/312; G01N 21/00
See application file for complete search history.

(56) References Cited

U.S. PATENT DOCUMENTS 5,573,727 A * 11/1996 Keefe ..................... G01N 1/312
                                                                118/423
2008/0193333 A1 * 8/2008 Takahashi ................ G01N 1/30
                                                                422/63

* cited by examiner

*Primary Examiner* — Jyoti Nagpaul
(74) *Attorney, Agent, or Firm* — Barry Choobin; Patent 360

(57) ABSTRACT

The embodiments herein provide a tissue processing and slide staining equipment with a three degree freedom robotic arm that simultaneously performs tissue processing and slide staining for several sample baskets with similar or different processing methods. The equipment comprises two dimensional array of cylindrical containers with lids to hold sample baskets in position. The arm moves freely in X, Y, and Z axis using rails and stepper motors. The arm is not connected to lids and baskets and accepts new baskets of samples while processing previous samples. The arm grips the basket containing samples and leaves the basket in proximity to the reagent. The equipment comprises a user friendly interface having appropriate callouts to guide a user during process programming/running. The interface allows the user to freely design and modify each step of the processing method. The equipment comprises an intelligent rule database that automatically handles human-induced errors.

19 Claims, 9 Drawing Sheets

TISSUE PROCESSING AND SLIDE STAINING APPARATUS WITH ROBOTIC ARM HAVING THREE DEGREES OF FREEDOM

The present invention is sponsored by Iranian National Science foundation (INSF).

BACKGROUND

1. Technical Field

The embodiments herein are generally related to a field of histology. The embodiments herein are particularly related to tissue processing and slide staining devices. The embodiments herein are more particularly related a tissue processing and slide staining equipment with a robotic arm having three degrees of freedom to perform tissue processing and slide staining simultaneously for several sample baskets with similar or different processing methods.

2. Description of the Related Art

Histology is a science associated with a processing of tissues for examination or analysis related to cellular morphology, chemical composition, tissue structure or composition or other tissue characteristics. The examination results are used by the pathologists to obtain an information about a cell structure and to diagnose illnesses. The tissue processing halts the degradation of cellular structure and stabilizes the cellular characteristics. Further, the tissue processing sufficiently hardens the tissue so that extremely fine segments are cut therefrom for an analysis purpose. Hence, the tissues taken from the body must be processed in the laboratory before the sample is analyzed for diagnostic or testing purposes. Fixation, dehydration, clearing and impregnation or infiltration are the four general steps that are performed during a processing of a tissue sample in the laboratory. These steps are effectuated by submerging the tissue samples in different solutions to produce chemical reactions. The tissue samples are processed in a qualitative and uniform manner such that the analytical results and diagnosis are consistent and accurate.

In general, the tissue processing cassettes or baskets are used for performing the biological tissue specimens. The tissue processing cassettes typically include a rectangular, box with an opening at the top side. the box has a base has a perforated bottom wall and a removable perforated cover or lid. The cassettes are made up of a moldable plastic to resist a damage or a reaction from the processing solvents and acids or reaction with the tissue specimen. The tissue specimen is typically placed within an enclosure formed by the base and lid. Later, the tissue specimen is processed in various solutions that are appropriate to the tissue and the examination.

In the conventional tissue processing equipment, the basket containing the tissue samples and the lids of containers are connected to a robotic arm which moves the sample basket from one container to another one. By connecting the basket and lids to the robotic arm, the conventional tissue processing equipment causes some crucial disadvantages in run time. The disadvantages include a limitation in processing a number of sample baskets that are simultaneously processed by the equipment. A pre-set number of containers, for example, less than 10 percent of the containers are utilized during a sequential process while other 90% which are filled with liquid/reagent remain useless. The equipment does not accept new samples while processing the previous samples. Due to these disadvantages, the laboratory faces serious problems in case of emergency.

The conventional tissue processing equipment usually utilizes higher volume containers to compensate for a low throughput caused by their sequential or limited parallel processing. As a result, these tissue processing equipment suffers from a low quality tissue processing and high liquid/reagent consumption problems. Low quality tissue processing problem is caused by keeping different kind of tissues with different absorption rates in one sample basket and running the same process for all of them. The high liquid/reagent consumption problem is caused due to an inefficient utilization or underutilization of the liquids used by high volume containers. In a conventional rotary tissue processing equipment, all the container lids are connected to the robotic arm. Hence, the container lids are frequently opened/closed unnecessarily for each move thereby leading to higher liquid evaporation and consumption. Also, the conventional fixation and dehydration methods of tissue specimens are time consuming and labor intensive when the tissues are processed manually. In some cases, these methods utilize potentially toxic substances which release malodorous vapor.

Hence there is a need for a tissue processing and slide staining equipment with a robotic arm having three degrees of freedom to simultaneously performs tissue processing and slide staining for several sample baskets with similar or different processing methods. Further, there is a need for a tissue processing and slide staining equipment with a three degree freedom movement robotic arm that is not connected to lids and baskets and which accepts new baskets of samples while processing or staining previous samples. Furthermore, there is a need for a tissue processing and slide staining equipment with a robotic arm having three degrees of freedom to provide a higher throughput when compared with the conventional tissue processors. There is also a need for a tissue processing and slide staining equipment with a robotic arm having three degrees of freedom to accept emergency samples without any conflicts with previous tissue processes. There is also a need for a tissue processing and slide staining equipment with a robotic arm having three degrees of freedom to reduce a liquid evaporation rate by eliminating unnecessary lid opening/closing operations. There is also a need for a tissue processor and a slide staining equipment with a robotic arm having three degrees of freedom to provide a user friendly interface having appropriate callouts to guide a user during programming/running process. There is also a need for a tissue processing and slide staining equipment with a three degree freedom movement robotic arm that automatically chooses a similar reagent container when the reagent station defined by the program is already occupied by another basket. There is also a need for tissue processing and slide staining equipment with a three degree freedom movement robotic arm that is capable of fixing a position of a lid on the container and prioritizing the tasks to avoid any possible conflicts. There is also a need for a tissue processing and slide staining equipment with a filtration system and an exhaust facility to prevent toxic gas emissions. There is also a need for a tissue processing and slide staining equipment equipped with standard signs and alarms to provide an indication to the user about the errors and to protect the user from any possible harm.

The above mentioned shortcomings, disadvantages and problems are addressed herein and which will be understood by reading and studying the following specification.

OBJECT OF THE EMBODIMENTS

The primary object of the embodiments herein is to provide a tissue processing and slide staining equipment with a three degree freedom movement robotic arm to perform tissue processing and slide staining simultaneously for several sample baskets with similar or different processing methods.

Another object of the embodiments herein is to provide a tissue processing and slide staining equipment with a three degree freedom movement robotic arm that is not connected to the lids and sample baskets and which accepts new sample baskets during a processing or staining of previous samples.

Yet another object of the embodiments herein is to provide a tissue processing and slide staining equipment with a three degree freedom movement robotic arm to provide a higher throughput when compared with the conventional tissue processors.

Yet another object of the embodiments herein is to provide a tissue processing and slide staining equipment with a robotic arm having three degrees of freedom to accept the emergency samples without any conflicts with previous tissue processes.

Yet another object of the embodiments herein is to provide a tissue processing and slide staining equipment with a robotic arm having three degrees of freedom to reduce a liquid evaporation rate by eliminating the unnecessary lid opening/closing operations.

Yet another object of the embodiments herein is to provide a need for a tissue processor and a slide staining equipment with a robotic arm having three degrees of freedom to provide a user friendly interface having appropriate callouts to guide a user during process programming/running.

Yet another object of the embodiments herein is to provide a tissue processing and slide staining equipment with a robotic arm having three degrees of freedom to automatically choose a similar reagent container when the reagent station defined by the program is already occupied by another sample basket.

Yet another object of the embodiments herein is to provide a tissue processing and slide staining equipment with a three degree freedom movement robotic arm that is capable of fixing a position of a lid on a container and prioritizing the tasks to avoid any possible conflicts.

Yet another object of the embodiments herein is to provide a tissue processing and slide staining equipment with an exhaust facility and a filtration system to prevent toxic gas emissions.

Yet another object of the embodiments herein is to provide a tissue processing and slide staining equipment with standard signs and alarms to provide an indication to the user about the errors and to protect the user from any possible harm.

These and other objects and advantages of the embodiments herein will become readily apparent from the following detailed description taken in conjunction with the accompanying drawings.

SUMMARY

The following details present a simplified summary of the embodiments herein to provide a basic understanding of the several aspects of the embodiments herein. This summary is not an extensive overview of the embodiments herein. It is not intended to identify key/critical elements of the embodiments herein or to delineate the scope of the embodiments herein. Its sole purpose is to present the concepts of the embodiments herein in a simplified form as a prelude to the more detailed description that is presented later.

The embodiments herein provide a tissue processing and slide staining system. The tissue processing and slide staining system comprises a chassis, a robotic arm mounted on the chassis, a gripper, a plurality of sample baskets to hold samples of tissue, a plurality of reagent containers with lids, a processor, a rule database, and a user interface. The robotic arm has three degrees of freedom movement. The gripper is placed at an end effector of the robotic arm. Each reagent container is filled with a liquid or reagent to process the samples of tissue. The processor is configured to control an operation and movement of the robotic arm based on a user defined program. The rule database stores a plurality of rules for controlling the operation and movement of the robotic arm based on the user defined program. The user interface is configured to receive the inputs and to enable a user to control a processing operation and movement of the robotic arm during process programming/running.

According to an embodiment herein, the processor is configured to perform a tissue processing operation and a slide staining operation simultaneously.

According to an embodiment herein, the processor is configured to perform a tissue processing operation and a slide staining operation of a plurality of sample baskets simultaneously with a similar or different processing programs.

According to an embodiment herein, the robotic arm is configured to move along X-axis, Y-axis, and Z-axis to insert a sample basket into a reagent container or to remove the sample basket from the reagent container.

According to an embodiment herein, the robotic arm is not connected to the lids of the container and the sample basket during a processing of the sample basket in the reagent container thereby enabling the robotic arm to move a rest of the plurality of sample baskets or a rest of the plurality of containers.

According to an embodiment herein, the robotic arm is configured to move in an upward direction along Z-axis to extract the sample basket from the container. The robotic arm is also configured to move in a downward direction along Z-axis to insert the sample basket into the cylindrical container. The robotic arm is also configured to move in forward or backward directions along X axis and Y-axis to move the sample basket from one position in an array to another position in the array.

According to an embodiment herein, the robotic arm is configured to handle or move new sample baskets during a tissue processing and staining of a sample in a sample basket under processing.

According to an embodiment herein, the robotic arm is further configured to fix a lid on one of the containers, when the lid is not positioned on the container.

According to an embodiment herein, the processor is configured to perform a new task of tissue processing while a sample basket comprising a tissue sample under processing is left inside one of the containers. The processor is also configured to prevent human-induced errors based on the rule database while processing the tissue samples. The processor is also configured to prioritize a plurality of processing tasks to avoid a conflict. The processor is also configured to process the emergency samples without any conflict or interference with a processing operation under progress. The processor is also configured to move the robotic arm to automatically choose a similar reagent container when a reagent station defined by a processing program is already engaged with another sample basket. The processor is also configured to halt a tissue processing operation, when the tissue processing operation under progress needs a specific reagent which does not exist in the containers. The processor is also configured to halt a tissue processing operation till the required reagent is available in the containers.

According to an embodiment herein, the user interface is configured to allow the user to freely design and modify each step of the tissue processing program or operation.

According to an embodiment herein, the tissue processing and slide staining system further comprises a plurality of rails, a plurality of stepper motors, a plurality of time chains, a plurality of wagons, and a plurality of spools to move the robotic arm in an upward direction and down ward direction along Z-axis and to move the robotic arm in left and right directions along X-axis and Y-axis.

According to an embodiment herein, the tissue processing and slide staining system further comprises an exhaust facility with a filtration system with to prevent toxic gases emission from the equipment during the tissue processing and slide staining.

According to an embodiment herein, the tissue processing and slide staining system further comprises standard signs and alarms to provide an alert or notification to the user regarding a plurality of errors and to protect the user from any possible harm.

According to an embodiment herein, the tissue processing and slide staining system further comprises a plurality of heating stations to adjust a temperature inside the containers to a preset value. The preset value is set by the user through the user interface.

According to an embodiment herein, the tissue processing and slide staining system further comprises a hydraulic door support jack, a battery box for supplying electrical power, an electronic board box for housing a processor, a memory and a data base, a plurality of movement sensors for detecting and controlling a movement of the robotic arm along X-axis, Y-axis, and Z-axis, a plurality of cable chains connected to the robotic arm, a paraffin temperature control unit for controlling a temperature inside the system, a solenoid valve, a plurality of legs for supporting the system/chassis, a margin, a plurality of spring pins for positioning the container and for adjusting a position of the containers, and a ventilation fan for exhausting the toxic gases and contaminants.

According to an embodiment herein, the gripper is designed and configured to grip and hold the sample baskets and lids.

According to an embodiment herein, the user interface is configured to displays choices of menus, buttons, dialogs, and callouts to guide the user to provide inputs during a programming of tissue processing and staining operations.

According to an embodiment herein, the user interface is configured to provide details related to a resident time or reaction of tissue sample with a reagent in the reaction container, sample basket shaking method and pattern inside the reagent container.

According to an embodiment herein, the processor is configured to adjust a reaction time and a shaking pattern and shaking duration of a sample basket outside the reagent container to control a reagent carry-over contamination.

According to an embodiment herein, the containers are designed to prevent an inadvertent opening of the lid during a tissue processing and staining operation.

According to an embodiment herein, the sample basket is configured and designed to hold the slides in a vertical manner and the slides are designed to hold the tissue samples.

According to an embodiment herein, the containers are designed and configured to wash the sample baskets with a running water.

According to an embodiment herein, the preset rules stored in the preset rule database are generated based on inputs received from a plurality of professional pathologists.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
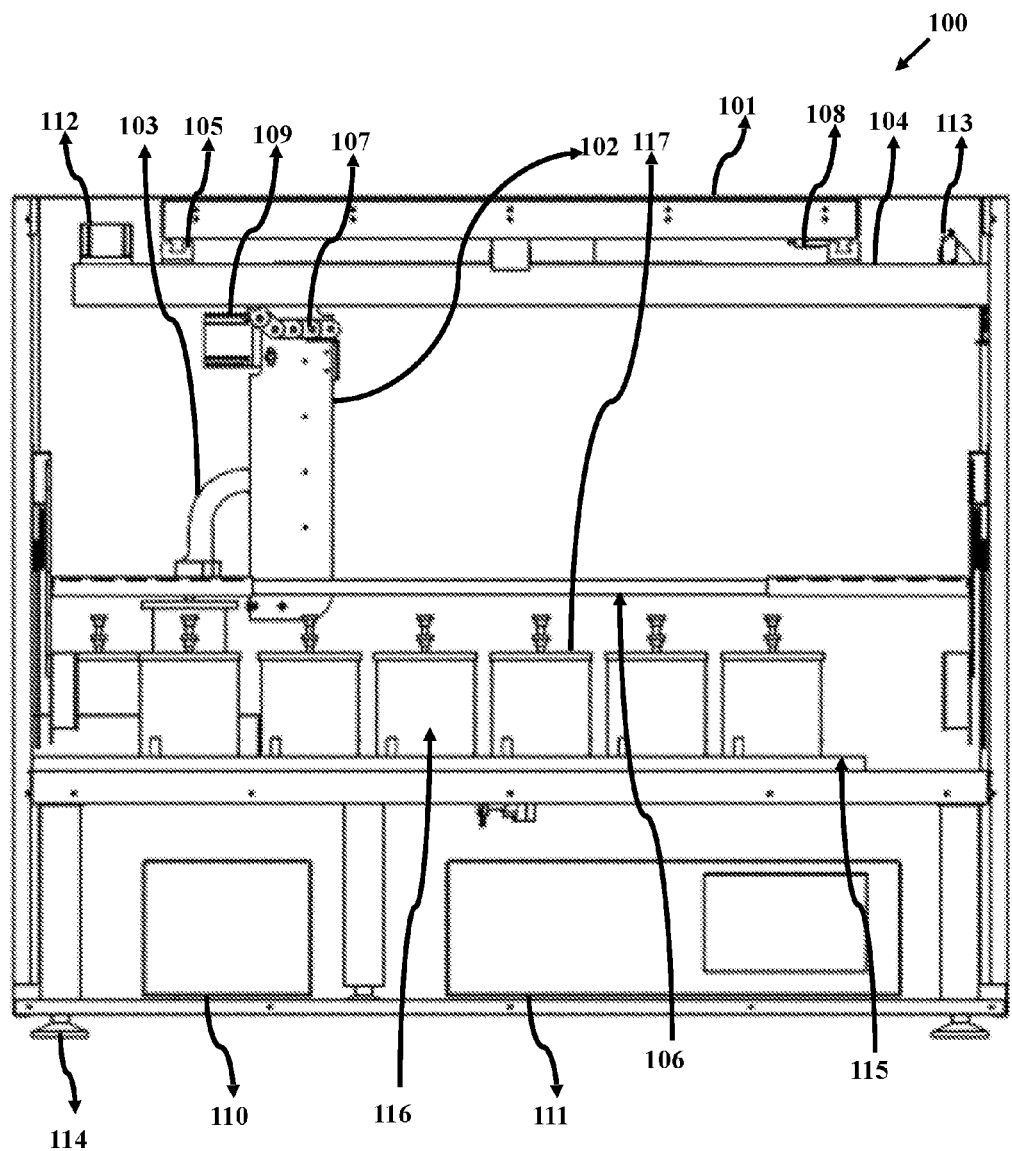
FIG. 1 illustrates a front side view of a tissue processing and slide staining equipment with a robotic arm having three degrees of freedom, according to an embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide a tissue processing and slide staining system. The tissue processing and slide staining system comprises a chassis, a robotic arm mounted on the chassis, a gripper, a plurality of sample baskets to hold samples of tissue, a plurality of reagent containers with lids, a processor, a rule database, and a user interface. The robotic arm has three degrees of freedom movement. The gripper is placed at an end effector of the robotic arm. Each reagent container is filled with a liquid or reagent to process the samples of tissue. The processor is configured to control an operation and movement of the robotic arm based on a user defined program. The rule database stores a plurality of rules for controlling the operation and movement of the robotic arm based on the user defined program. The user interface is configured to receive the inputs and to enable a user to control a processing operation and movement of the robotic arm during process programming/running.

According to an embodiment herein, the processor is configured to perform a tissue processing operation and a slide staining operation simultaneously.

According to an embodiment herein, the processor is configured to perform a tissue processing operation and a slide staining operation of a plurality of sample baskets simultaneously with a similar or different processing programs.

According to an embodiment herein, the robotic arm is configured to move along X-axis, Y-axis, and Z-axis to insert a sample basket into a reagent container or to remove the sample basket from the reagent container.

According to an embodiment herein, the robotic arm is not connected to the lids of the container and the sample basket during a processing of the sample basket in the reagent container thereby enabling the robotic arm to move a rest of the plurality of sample baskets or a rest of the plurality of containers.

According to an embodiment herein, the robotic arm is configured to move in an upward direction along Z-axis to extract the sample basket from the container. The robotic arm is also configured to move in a downward direction along Z-axis to insert the sample basket into the cylindrical container. The robotic arm is also configured to move in forward or backward directions along X axis and Y-axis to move the sample basket from one position in an array to another position in the array.

According to an embodiment herein, the robotic arm is configured to handle or move new sample baskets during a tissue processing and staining of a sample in a sample basket under processing.

According to an embodiment herein, the robotic arm is further configured to fix a lid on one of the containers, when the lid is not positioned on the container.

According to an embodiment herein, the processor is configured to perform a new task of tissue processing while a sample basket comprising a tissue sample under processing is left inside one of the containers. The processor is also configured to prevent human-induced errors based on the rule database while processing the tissue samples. The processor is also configured to prioritize a plurality of processing tasks to avoid a conflict. The processor is also configured to process the emergency samples without any conflict or interference with a processing operation under progress. The processor is also configured to move the robotic arm to automatically choose a similar reagent container when a reagent station defined by a processing program is already engaged with another sample basket. The processor is also configured to halt a tissue processing operation, when the tissue processing operation under progress needs a specific reagent which does not exist in the containers. The processor is also configured to halt a tissue processing operation till the required reagent is available in the containers.

According to an embodiment herein, the user interface is configured to allow the user to freely design and modify each step of the tissue processing program or operation.

According to an embodiment herein, the tissue processing and slide staining system further comprises a plurality of rails, a plurality of stepper motors, a plurality of time chains, a plurality of wagons, and a plurality of spools to move the robotic arm in an upward direction and down ward direction along Z-axis and to move the robotic arm in left and right directions along X-axis and Y-axis.

According to an embodiment herein, the tissue processing and slide staining system further comprises an exhaust facility with a filtration system with to prevent toxic gases emission from the equipment during the tissue processing and slide staining.

According to an embodiment herein, the tissue processing and slide staining system further comprises standard signs and alarms to provide an alert or notification to the user regarding a plurality of errors and to protect the user from any possible harm.

According to an embodiment herein, the tissue processing and slide staining system further comprises a plurality of heating stations to adjust a temperature inside the containers to a preset value. The preset value is set by the user through the user interface.

According to an embodiment herein, the tissue processing and slide staining system further comprises a hydraulic door support jack, a battery box for supplying electrical power, an electronic board box for housing a processor, a memory and a data base, a plurality of movement sensors for detecting and controlling a movement of the robotic arm along X-axis, Y-axis, and Z-axis, a plurality of cable chains connected to the robotic arm, a paraffin temperature control unit for controlling a temperature inside the system, a solenoid valve, a plurality of legs for supporting the system/chassis, a margin, a plurality of spring pins for positioning the container and for adjusting a position of the containers, and a ventilation fan for exhausting the toxic gases and contaminants.

According to an embodiment herein, the gripper is designed and configured to grip and hold the sample baskets and lids.

According to an embodiment herein, the user interface is configured to displays choices of menus, buttons, dialogs, and callouts to guide the user to provide inputs during a programming of tissue processing and staining operations.

According to an embodiment herein, the user interface is configured to provide details related to a resident time or reaction of tissue sample with a reagent in the reaction container, sample basket shaking method and pattern inside the reagent container.

According to an embodiment herein, the processor is configured to adjust a reaction time and a shaking pattern and shaking duration of a sample basket outside the reagent container to control a reagent carry-over contamination.

According to an embodiment herein, the containers are designed to prevent an inadvertent opening of the lid during a tissue processing and staining operation.

According to an embodiment herein, the sample basket is configured and designed to hold the slides in a vertical manner and the slides are designed to hold the tissue samples.

According to an embodiment herein, the containers are designed and configured to wash the sample baskets with a running water.

According to an embodiment herein, the preset rules stored in the preset rule database are generated based on inputs received from a plurality of professional pathologists.

FIG. 1 illustrates a front view of a tissue processing and slide staining equipment with a three degree freedom movement robotic arm, according to an embodiment herein. With respect to FIG. 1, the front view of the tissue processing and slide staining equipment 100 comprises main body 101, robotic arm 102, gripper 103, chassis 104, rail-C 105, hydraulic door support jack 106, cable chain 107, movement sensor-A 108, stepper motor-A 109, battery box 110, electric boards box 111, stepper motor-B 112, right movement sensor-B 113, a plurality of legs 114, margin 115, a plurality of sample baskets and sliding cassettes, and a processor. The tissue processing and slide staining equipment 100 further comprises a two dimensional array of cylindrical containers 116 with lids 117 to hold the sample baskets in position. Each container 116 is either empty or filled with a specific liquid/reagent required for processing the tissue. The lids 117 act as a removable top cover for the containers 116. The sample baskets and the sliding cassettes are specially designed to hold the tissues of different sizes on the slides vertically in the containers 116.

According to an embodiment herein, the robotic arm 102 has three degrees of freedom and movement. The robotic arm is configured to move freely in X, Y, and Z axis. The robotic arm 102 is not connected to the lids 117 and the sample baskets placed in the equipment 100. The gripper 103 is designed and placed at the end effector of the robotic arm 102. The robotic arm 102 uses the gripper 103 to properly hold the sample baskets and the lids 117.

According to an embodiment herein, the robotic arm 102 is configured to move in Z-axis in an upward direction to extract a sample basket from the container 116. The robotic arm 102 is configured to move in Z-axis in a downward direction to insert a sample basket into the container 116. The robotic arm 102 is configured to move in X axis and Y axis in forward and backward directions to move the sample baskets from one position in an array to another array based on the processing method defined by the user.

According to an embodiment herein, the rail-C 105 is configured to move the robotic arm 102 in forward and backward directions along the Y axis. The stepper motor-A 109 is configured to move the robotic arm 102 in upward and downward directions along Z axis. The stepper motor-B 112 is configured to move the robotic arm 102 in left and right directions along X axis.

According to an embodiment herein, the processor is configured to control the operation and movement of the robotic arm based on the tissue processing method defined by the user. The processor is also configured to process a new tissue sample while a tissue sample under-processing is left inside a container. The processor is also configured to use a rule database to prevent human-induced errors during the processing of the tissue samples. The processor is also configured to prioritize a plurality of processing tasks to avoid any possible conflicts. For instance, the slide staining process has a priority over the tissue processing operation. A priority is given to a shaking process of a sample basket under-processing instead of moving another sample basket from one station to another station. The processor is also configured to accept the emergency samples without any conflicts with a previous process. The processor is also configured to automatically choose a similar reagent container when a reagent station defined by the program is already occupied by another sample basket. The processor is also configured to halt the tissue processing operation when a specific reagent which does not exist in the cylindrical containers is required. The processor is configured to halt the tissue processing operation, till the required reagent is available in the cylindrical containers.

According to an embodiment herein, the robotic arm 102 is configured to grip the sample basket containing tissue samples with the gripper 103. Later, the robotic arm is configured to extract the sample basket from the reagent container 116. The robotic arm 102 is configured to move the extracted basket to a next container based on a user defined program, through a three degree movement relative to the next reagent container position. Further, the robotic arm 102 is configured to leave the basket in the proximity of the reagent in the next reagent container for a predefined time. During this time, the robotic arm 102 is configured to continuously move or rearrange other sample baskets from one reagent container to other reagent containers based on the pre-defined program set by the user.

According to an embodiment herein, a plurality of rules is developed with the knowledge of professional pathologists to avoid human-induced errors during the processing of tissue samples. These rules are stored in a database and are installed in the tissue processing and slide staining equipment 100 to prevent possible human errors during a tissue processing operation.

According to an embodiment herein, the containers 116 are specially designed for easy disposal. The containers are designed in such a manner to prevent an unwanted opening of the lids of other containers that are not in use. The containers 116 are also configured to wash the sample baskets with a running water.

According to an embodiment herein, the tissue processing and slide staining equipment 100 comprises a user friendly interface to allow a user to design or define a processing method for each sample basket. The interface provides options of menus, buttons, dialogs, and appropriate callouts to guide the user during programming/running process. The interface allows the user to freely design and modify each and every detail in each step of the tissue processing method. The details include a duration of tissue-reagent resident time or tissue-reagent reaction time, a shaking pattern of samples inside the liquid or reagent container, etc. According to an embodiment herein, human-robot interaction techniques are considered/used to optimize the efficiency of the robotic arm, while designing the user-friendly interface. Thus, the interface allows the user to freely adapt the equipment 100 with respect to the process requirements.

According to an embodiment herein, the user-friendly interface allows the user to define a plurality of mixing methods for the floating samples in the reagent containers. This further leads to improve the absorption and process efficiency. Also, the user-friendly interface allows the user to program the resident time or reaction time of the samples with liquids or reagents to maximize the efficiency of the process.

According to an embodiment herein, the tissue processing and slide staining equipment 100 is configured to have adequate memory to store a plurality of user designed/defined tissue processing or staining programs. The interface allows the user to define a number of steps for replacing the sample baskets between the reagent containers in each program. The interface also allows the user to define the resident time sample in a reagent container for each sample basket.

According to an embodiment herein, the tissue processing and slide staining equipment 100 is configured to perform a plurality of processing methods for a plurality of sample baskets simultaneously. The plurality of the processing methods adapted/followed for the plurality of sample baskets are mutually different. As a result, the equipment 100 achieves a significantly higher throughputs when compared with the conventional tissue processing equipment.

According to an embodiment herein, the evaporation of liquid or reagent is reduced to a high extent by eliminating the unnecessary lid opening/closing operations. Hence, the liquid or reagent consumption is low. Also, the tissue processing and slide staining equipment 100 does not require extra high volume containers to compensate for the throughputs.

According to an embodiment herein, the tissue processing and slide staining equipment 100 requires a minimum carryover between the liquids or reagents thereby leading to less contamination due to reagent carryover process. Further, the carryover contamination is controlled by adjusting the shaking duration and method of samples (sample baskets) outside the container before moving the sample in the container-A into container B using the robotic arm.

According to an embodiment herein, the robotic arm 102 is configured to fix the position of the lid 117 on container when the lid 117 is not positioned properly on the cylindrical container 116.

According to an embodiment herein, the tissue processing and slide staining equipment 100 comprises an exhaust facility with a filtration system to prevent an emission of toxic gases during tissue processing and slide staining operation. Further, the equipment 100 allows the user to optionally use appropriate filters to prevent the emission of toxic gases during tissue processing.

According to an embodiment herein, the tissue processing and slide staining equipment 100 is fully closed to prevent a toxic gas emission.

According to an embodiment herein, the tissue processing and slide staining equipment 100 comprises standard signs and alarms to provide an indication/alarm/notification to the user regarding the errors and to protect the user from any possible harm.

According to an embodiment herein, the tissue processing and slide staining equipment 100 comprises a plurality of heating stations to provide a required/necessary temperature inside the tissue processing and slide staining equipment 100.

According to an embodiment herein, the tissue processing and slide staining equipment 100 is configured to prioritize a mixing of the samples in a basket and reagents in a container over replacing of samples in other sample baskets. Also, the equipment 100 is configured to prioritize the replacement of the sample basket that entered first in the queue.

Figure 2:
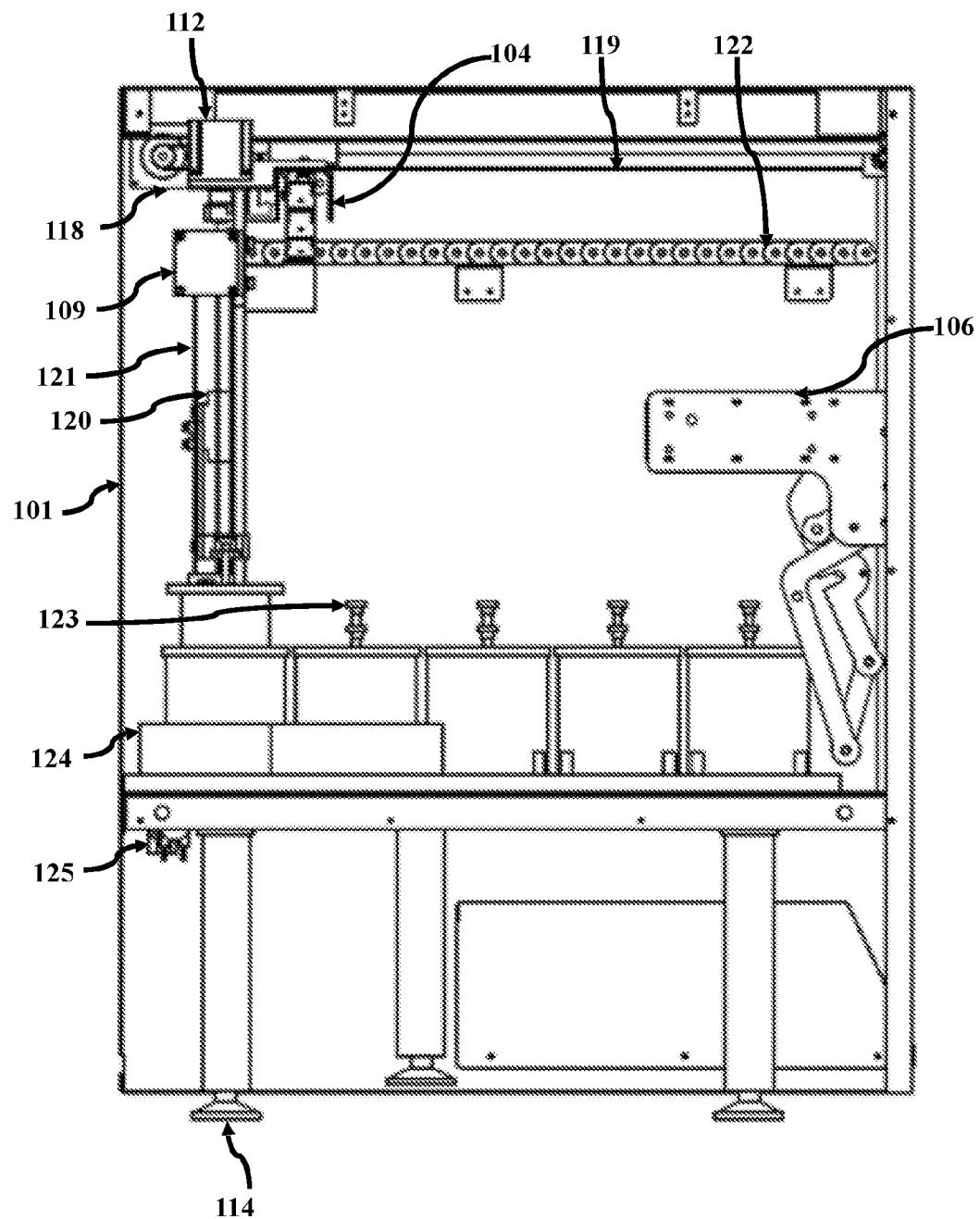
FIG. 2 illustrates a side view of a tissue processing and slide staining equipment with a three degree freedom movement robotic arm, according to an embodiment herein.

FIG. 2 illustrates a side view of a tissue processing and slide staining equipment with a robotic arm having three degrees of freedom, according to an embodiment herein. With respect to FIG. 2, the side view of the tissue processing and slide staining equipment comprises main body 101, chassis 104, hydraulic door support jack 106, stepper motor (A) 109, stepper motor (B) 112, leg 114, stepper motor (C) 118, time chain (C) 119, wagon (A) 120, time chain (A) 121, cable chain 122, paraffin temperature control unit 124, solenoid value 125 and knob lid 123.

According to an embodiment herein, the stepper motor (A) 106 is configured to move the robotic arm in upward and downward directions along Z-axis. The stepper motor (B) 112 is configured to move the robotic arm in left and right directions along X-axis. The stepper motor (C) 118 is configured to move the robotic arm in forward and backward directions along Y-axis. The time chain (C) 119 is configured to move the robotic arm in forward and backward directions along Y-axis. The wagon (A) 120 is configured to move the robotic arm in up and down directions along the Z-axis. The time chain (A) 121 is configured to move the robotic arm in upward and downward directions along the Z-axis. The paraffin temperature control unit 124 comprises heating stations that are configured to provide necessary temperature inside the tissue processing and slide staining equipment.

Figure 3:
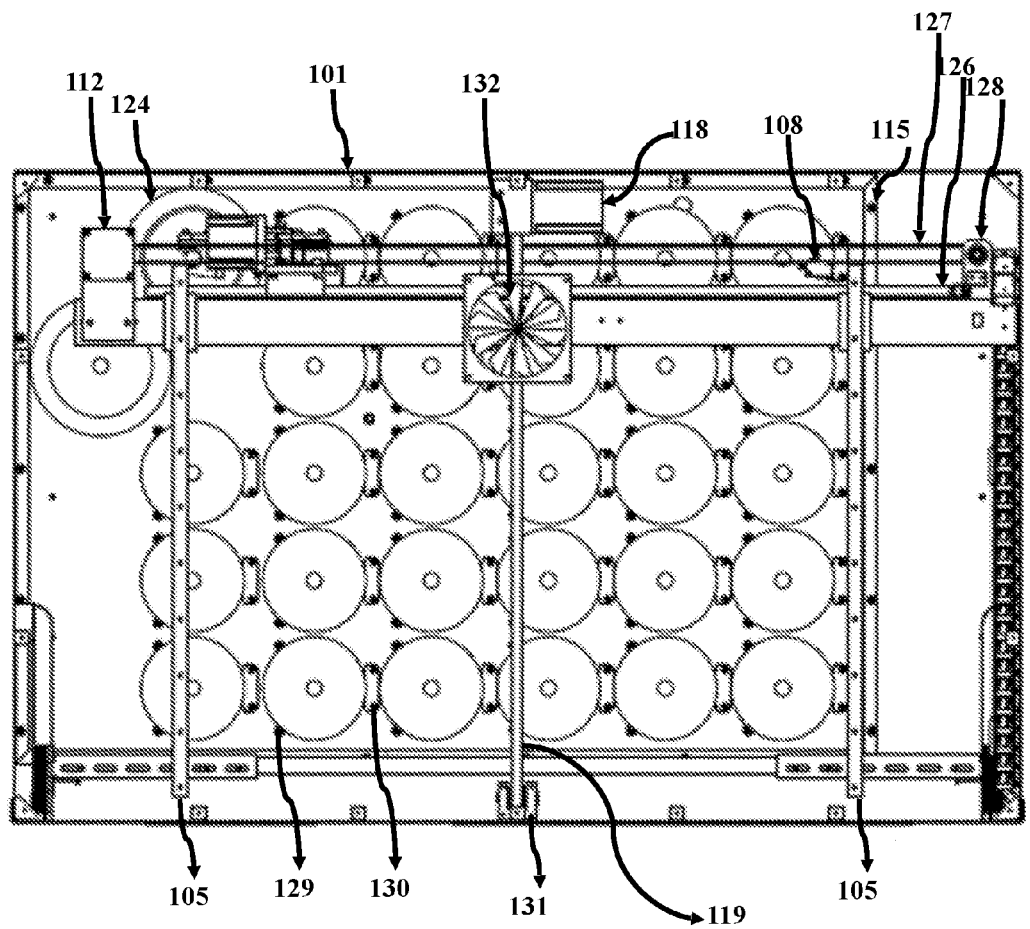
FIG. 3 illustrates a top side view of a tissue processing and slide staining equipment with a three degree freedom movement robotic arm, according to an embodiment herein.

FIG. 3 illustrates a top view of a tissue processing and slide staining equipment with a three degree movement robotic arm, according to an embodiment herein. With respect to FIG. 3, the top view of the tissue processing and slide staining equipment comprises body 101, rail (C) 105, movement sensor (A) 108, stepper motor (B) 112, margin 115, stepper motor (C) 118, time chain (C) 119, paraffin temperature control unit 124, rail (B) 126, time chain (B) 127, spool (B) 128, pin 129, spring pin 130, spool (C) 131, and ventilation fan 132.

According to an embodiment herein, rail (C) 105 is configured to move the robotic arm in forward and backward directions along the Y-axis. The stepper motor (B) 112 is configured to move the robotic arm in left and right directions along the X-axis. The stepper motor (C) is configured to move the robotic arm in forward and backward directions along the Y-axis. The time chain (C) 119 is configured to move the robotic arm in forward and backward directions along the Y-axis. The paraffin temperature control unit 124 comprises heating stations that are configured to provide necessary temperature inside the tissue processing and slide staining equipment. The rail (B) 126 is configured to move the robotic arm in left and right directions along the X-axis. The time chain (B) 127 is configured to move the robotic arm in left and right directions along the X-axis. The spool (B) 128 is configured to move the robotic arm in left and right directions along the X-axis. The pin 129 and the springy pin 130 are used to fix the container position and are configured to prevent the movement of the container during tissue processing and slide staining. The spool (C) 131 is configured to move the robotic arm in forward and backward directions along the Y-axis.

Figure 4:
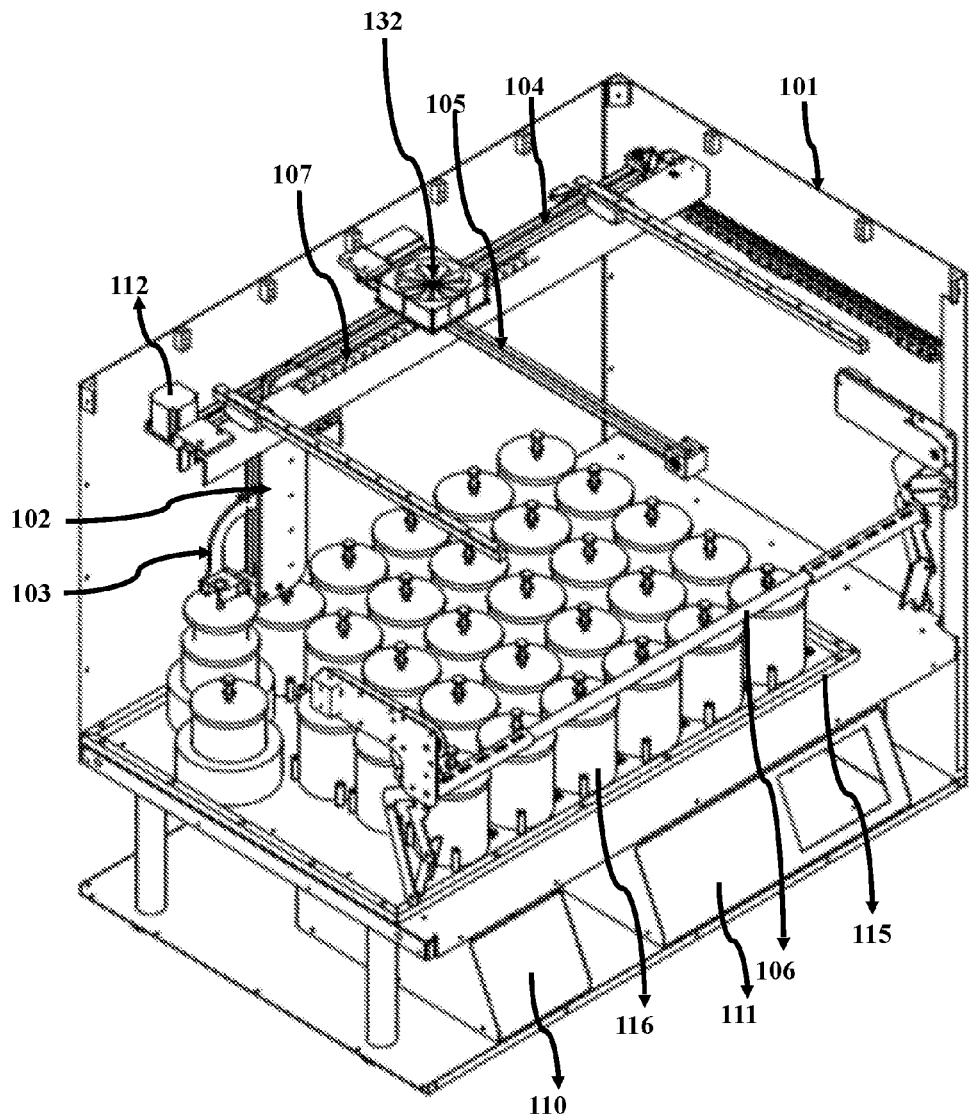
FIG. 4 illustrates a top side perspective view of a tissue processing and slide staining equipment with a robotic arm having three degrees of freedom, according to an embodiment herein.

FIG. 4 illustrates top perspective view of a tissue processing and slide staining equipment with a three degree movement robotic arm, according to an embodiment herein. With respect to FIG. 4, the angular top view of the tissue processing and slide staining equipment comprises body 101, robotic arm 102, gripper 103, chassis 104, rail (C) 105, hydraulic door support jack 106, cable chain 107, battery box 110, electric board box 111, stepper motor (B) 112, margin 115, and a plurality of cylindrical containers 116. The battery box 110 provides necessary electrical power required for the functioning of the equipment 100.

Figure 5:
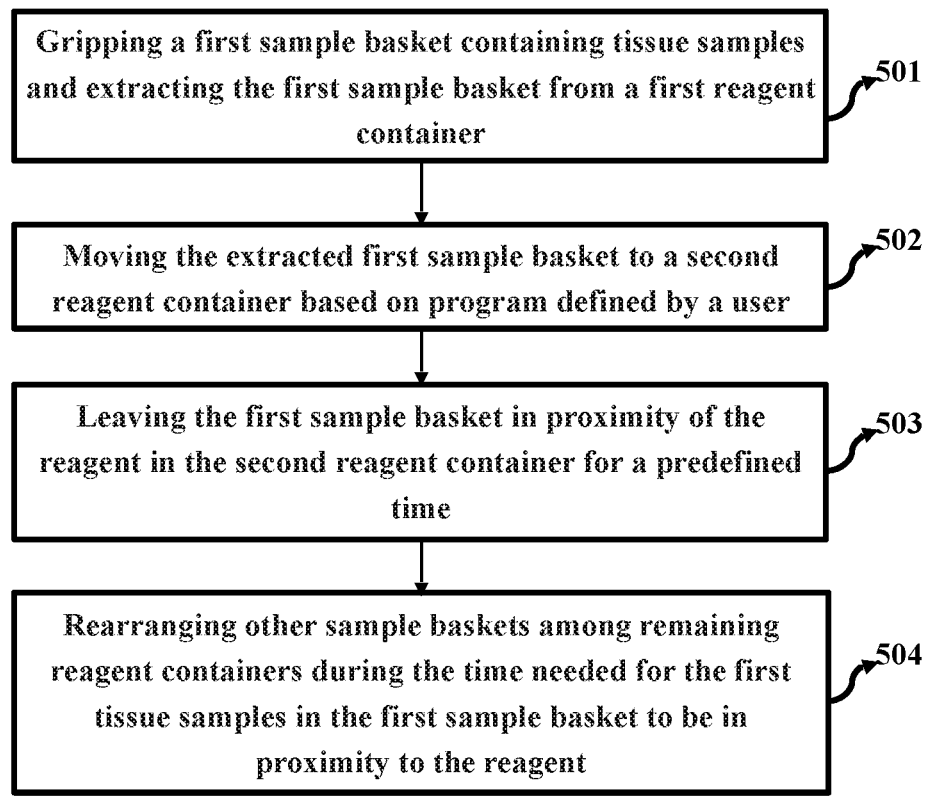
FIG. 5 illustrates a flowchart explaining a method of performing tissue processing and slide staining simultaneously using a tissue processing and slide staining equipment with a three degree freedom movement robotic arm, according to one embodiment of the present invention.

FIG. 5 illustrates a flowchart explaining a method of simultaneously performing tissue processing and slide staining using a tissue processing and slide staining equipment with a robotic arm having three degrees of freedom, according to one embodiment of the present invention. Initially, the robotic arm grips a first sample basket containing tissue samples with a gripper and then extracts the first sample basket from a first reagent container (step 501). The robotic arm moves the extracted first sample basket to a second reagent container based on a program defined by the user through a three dimensional movement relative to the second reagent container position (step 502). Further, the robotic arm leaves the first sample basket in the proximity of the reagent in the second reagent container for a predefined time (step 503). During this time, the robotic arm continuously move or rearrange remaining sample baskets among other reagent containers based on the program defined by the user (step 504).

Figure 6:
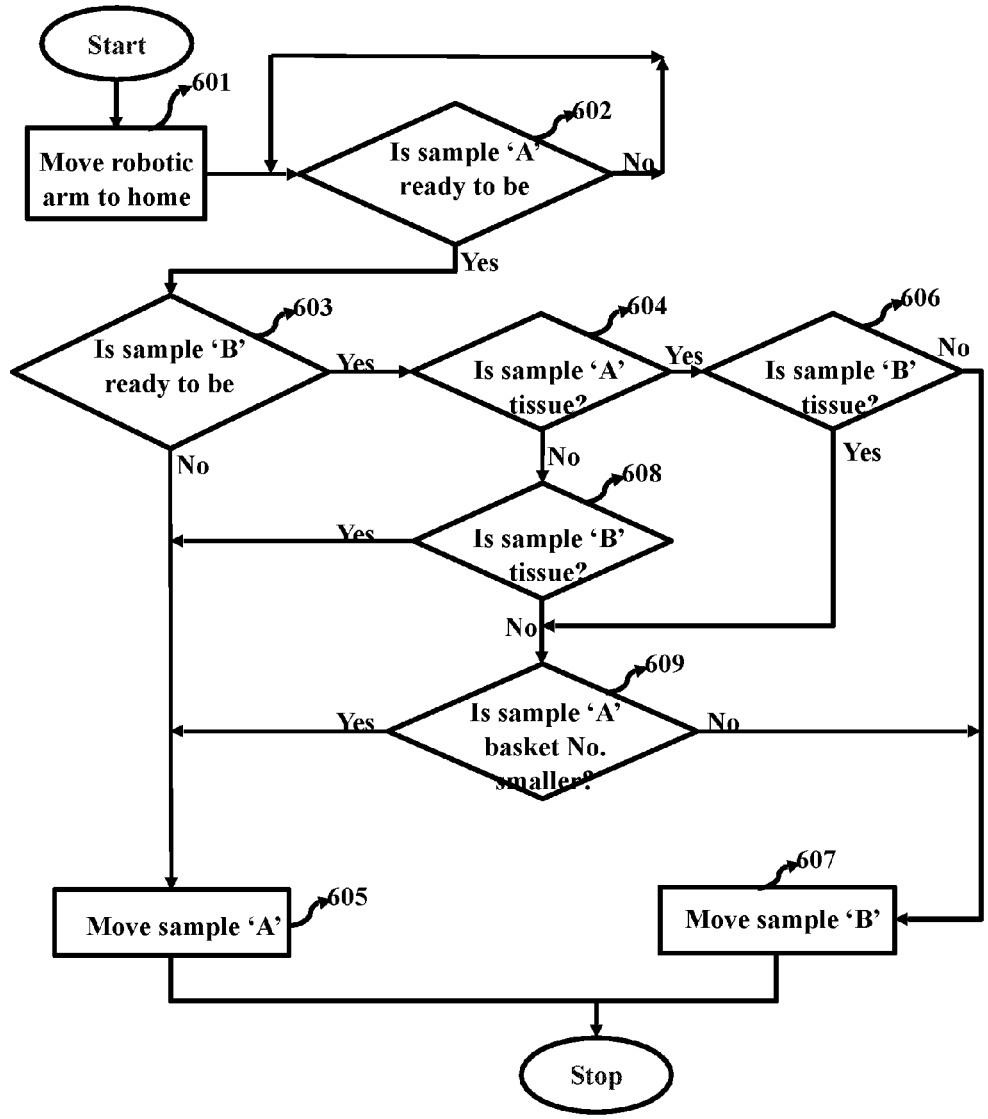
FIG. 6 illustrates a flowchart explaining a method of moving tissue sample A and tissue sample B in a tissue processing and slide staining equipment with a three degree freedom movement robotic arm, according to an embodiment herein.

FIG. 6 illustrates a flowchart explaining a method of moving sample 'A' and sample 'B' in a tissue processing and slide staining equipment with a three degree freedom movement robotic arm, according to an embodiment herein. Initially, the processor moves the three degree freedom movement robotic arm to a home position (step 601). Then, the processor checks whether the sample 'A' is ready to be replaced with another sample (step 602). When the sample 'A' is ready to be replaced, the processor checks whether the sample 'B' is ready to be replaced with another sample simultaneously (step 603). When the sample 'A' is not ready for the replacement, the processor checks again whether the sample 'A' is ready to be replaced with another sample.

When the sample 'B' is ready to be replaced with another sample simultaneously, the processor checks whether the sample 'A' is a tissue sample (step 604). When the sample 'B' is not ready to be replaced with another sample, the processor moves the sample 'A' using the robotic arm (step 605). When the sample 'A' is a tissue, the processor checks whether the sample 'B' is a tissue (step 606). When the sample 'B' is not a tissue, the processor moves sample 'B' using the three degree freedom robotic arm (step 607). When the sample 'A' is not a tissue, the processor checks whether the sample 'B' is a tissue (step 608). When the sample 'B' is a tissue, the processor moves the sample 'A' using the three degree freedom robotic arm (step 605). When the sample 'B' is not a tissue, the processor checks whether the number of samples in the sample basket A is smaller than the number of samples in the sample basket B (step 609). When the number of samples in the sample basket A is smaller than the number of samples in the sample basket B, then the processor moves the sample basket A using the robotic arm (step 605). When the number of samples in the sample basket A is larger than the number of samples in the sample basket B, the processor moves the sample basket B (step 607) using the robotic arm.

Figure 7:
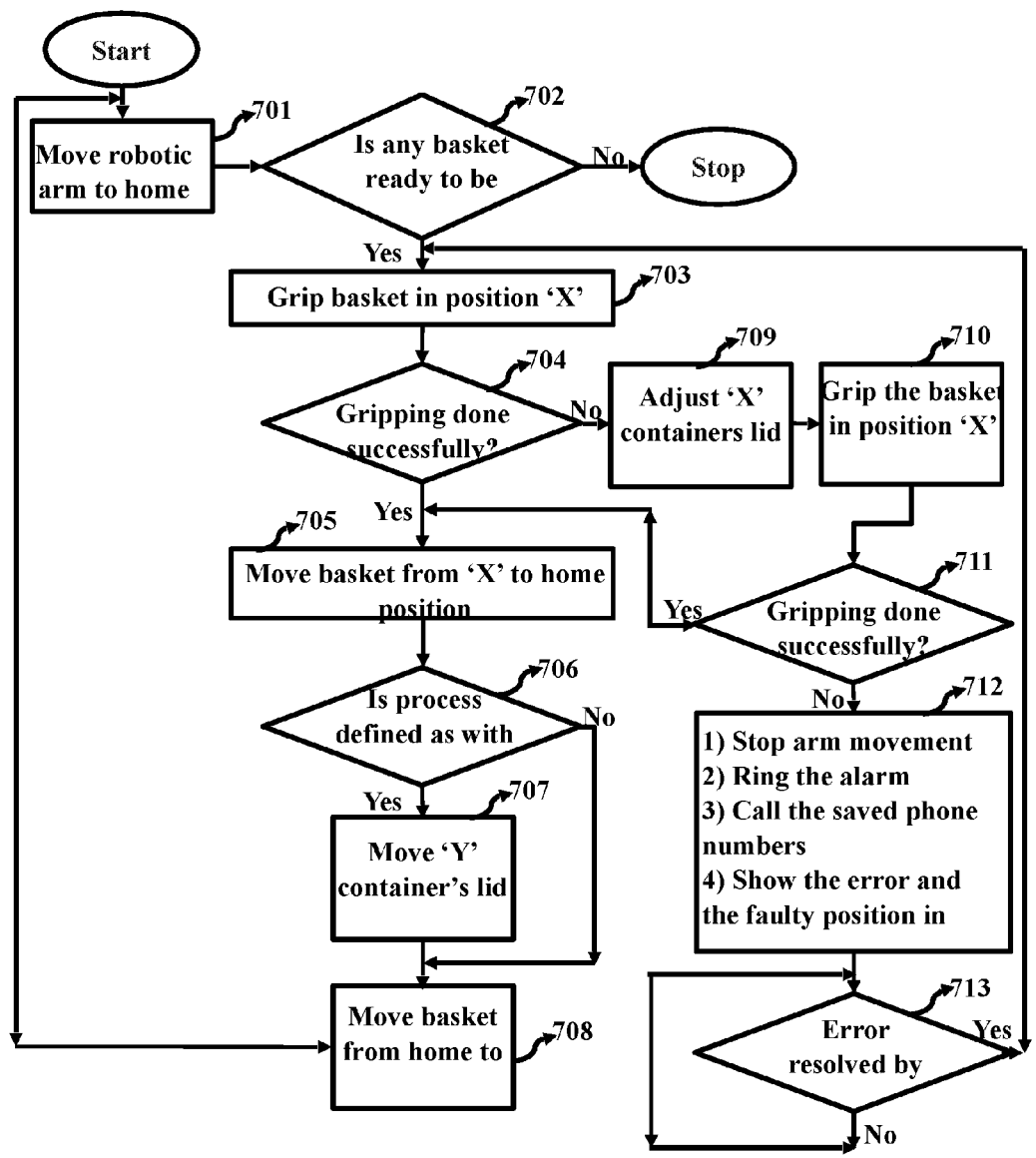
FIG. 7 illustrates a flowchart explaining a method of moving a basket from position X to position Y in a tissue processing and slide staining equipment with a three degree freedom movement robotic arm, according to an embodiment herein.

FIG. 7 illustrates a flowchart explaining a method of moving a basket from position 'X' to position 'Y' in a tissue processing and slide staining equipment with a three degree freedom movement robotic arm, according to an embodiment herein. Initially, the processor moves the three degree freedom movement robotic arm to a home position (step 701). Then, the processor checks whether any basket is ready to be replaced with another basket (step 702). When a basket is ready to be replaced, the processor allows the robotic arm to grip the basket in 'X' position (step 703). Further, the processor checks whether the gripping of the basket is done successfully (step 704). When the gripping is successful, the processor allows the robotic arm to move the basket from 'X' position to the home position (step 705). Later, the processor checks whether the process is defined as 'with lid' (step 706). When the process is defined as 'with lid', the processor allows the robotic arm to move the 'Y' container's lid to 'X' position (step 707). Further, the robotic arm moves the basket from home position to 'Y' position (step 708).

When the gripping of the basket is not successful, the processor allows the robotic arm to adjust the 'X' container's lid position (step 709). After adjusting the lid position, the processor allows the robotic arm to grip the basket in 'X' position (step 710). Further, the processor checks again whether the gripping of the basket is done successfully (step 711). When the gripping is successful, the control of the equipment executes from step 705. When the gripping of the basket is not successful, the equipment stops the robotic arm movement and displays the error and the fault position to the user through a user interface. Further, the processor triggers an alarm to indicate the error to the user. The processor also initiates a phone call to save the phone numbers to indicate the error (step 712). Later, the processor checks whether the error is resolved by the user (step 713). When the error is resolved, the control of the equipment executes from step 703.

Figure 8A:
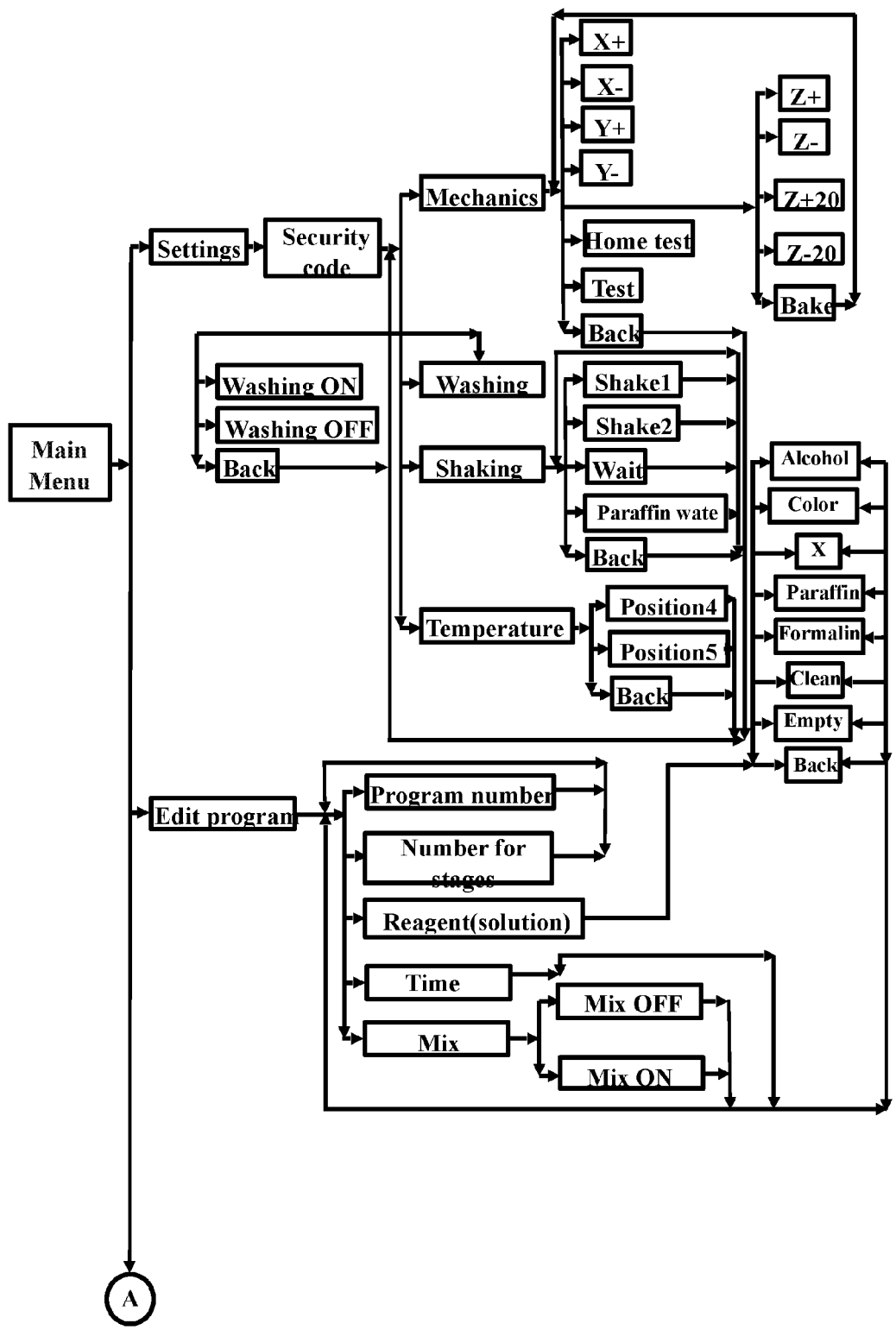
FIG. 8A and FIG. 8B collectively illustrate a flowchart explaining the overall functioning of a tissue processing and slide staining equipment, according to one embodiment herein.
Figure 8B:
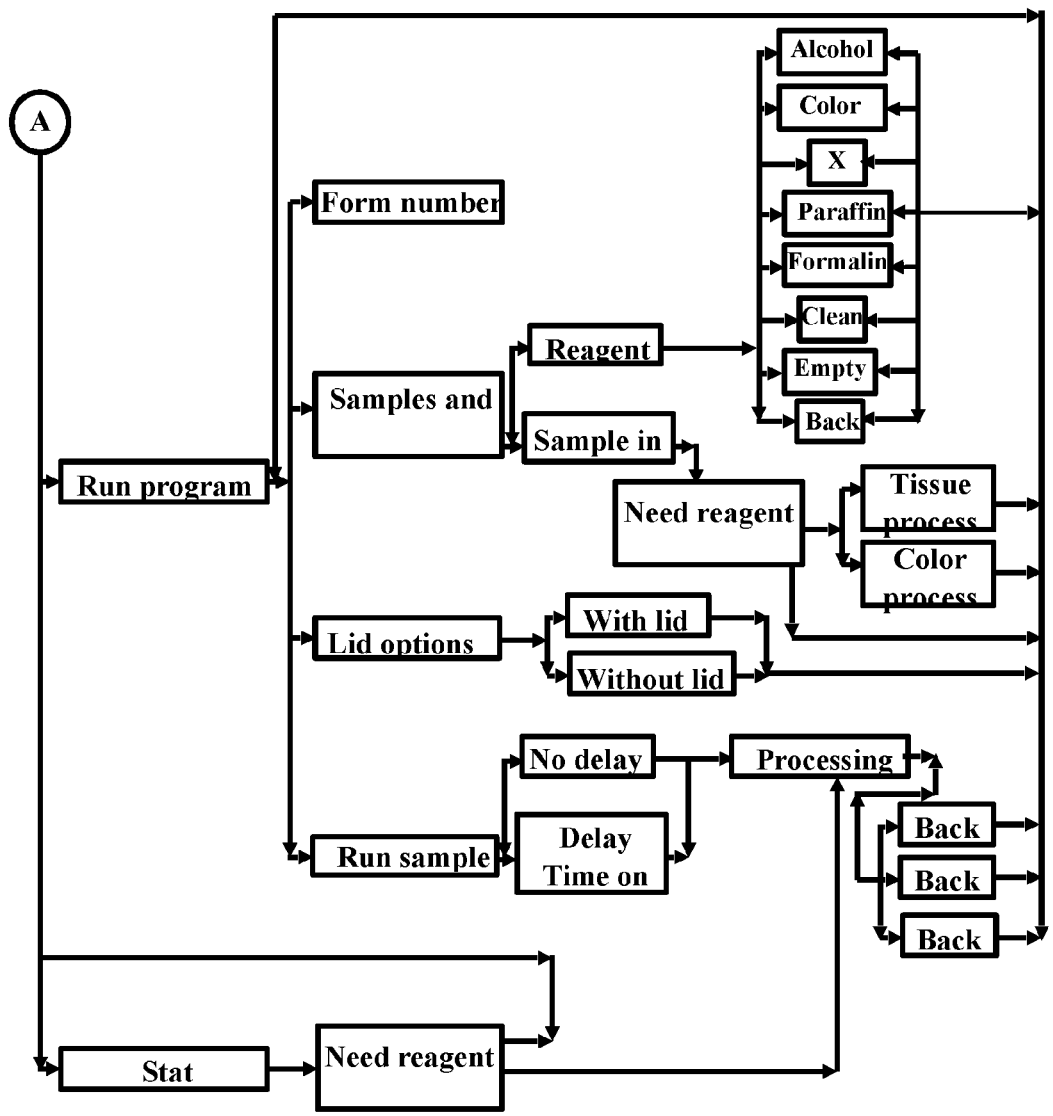

FIG. 8A and FIG. 8B collectively illustrate a flowchart explaining the overall functioning of a tissue processing and slide staining equipment, according to one embodiment of the present invention. The equipment comprises a user friendly interface having appropriate callouts to guide a user during programming/running process. The interface comprises choices of menus, buttons, and dialogs. The main menu comprises a plurality of options to freely design and modify each step of the tissue processing method. These options include 'settings', 'edit program', 'run program' and 'start'. The 'settings' option further include a plurality of sub menus to define tissue processing method for each basket. According to an embodiment herein, the equipment allows a user to access the settings after validating the user identity. The user needs to provide a valid security code to access the plurality of sub-menus in settings. The sub-menus of the 'settings' option include mechanics, washing, shaking, and temperature. The mechanics sub-menu allows the user to define the movement of the three degree freedom robotic arm. The washing sub-menu allows the user to start and stop a washing process of the baskets with running water. The shaking sub-menu allows the user to define number of shakes required for the basket while processing the tissues. The temperature sub-menu allows the user to control temperature inside the basket.

The 'edit program' option further includes a plurality of sub options that allows the user to edit a processing method. The sub options include program number, number of stages, reagent or solution, time, and mix. The reagent option further includes a plurality of options that allows the user to choose a reagent for tissue processing. The reagent options include alcohol, color, paraffin, formalin, and so on.

The 'run program' option further includes a plurality of sub options that allows the user to run a processing method in the equipment. The sub options of the 'run program' include form number, samples and reagent chart, lid option, and run sample. The lid options allow the user to run the tissue processing with lid or without lid on the container. The 'run sample' option allows the user to run the program with delay time or without a delay time. The stat option slows the user to process emergency tissue samples without any conflicts with previous the tissue processes.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A tissue processing and slide staining system, the system comprising:
    a chassis;
    a robotic arm mounted on the chassis, wherein the robotic arm has three degrees of freedom movement;
    a gripper, wherein the gripper is placed at an end effector of the robotic arm;
    a plurality of sample baskets to hold samples of tissue;
    a plurality of reagent containers with lids, wherein each reagent container is filled with a liquid or reagent to process the samples of tissue;
    a processor configured to control an operation and movement of the robotic arm based on a user defined program;
    a rule database for storing a plurality of rules for controlling an error in the tissue processing operation and staining process; and
    a user interface, wherein the user interface is configured to receive inputs and to enable a user to control the tissue processing operation, staining process and a movement of the robotic arm;
    wherein the processor is configured to perform a tissue processing operation and a slide staining operation simultaneously, and wherein the processor is configured to perform a tissue processing operation and a slide staining operation of a plurality of sample baskets simultaneously with a similar or different processing programs, and wherein the robotic arm is configured to move along X-axis, Y-axis, and Z-axis to insert a sample basket into a reagent container or to remove the sample basket from the reagent container, and wherein the robotic arm is not connected to the lids of the container and the sample basket during a processing of the sample in the reagent container thereby enabling the robotic arm to move a rest of the plurality of sample baskets or a rest of the plurality of containers.

2. The system according to claim 1, wherein the robotic arm is configured to move in an upward direction along Z-axis to extract the sample basket from the container, and wherein the robotic arm is configured to move in a downward direction along Z-axis to insert the sample basket into the cylindrical container, and wherein the robotic arm is configured to move in forward or backward directions along X and Y-axis to move the sample basket from one position in an array to another position in the array.

3. The system according to claim 1, wherein the robotic arm is configured to handle or move new sample baskets during a tissue processing and staining of a sample in a sample basket under processing.

4. The equipment according to claim 1, wherein the robotic arm is further configured to fix a lid on one of the containers, when the lid is not positioned on the container.

5. The system according to claim 1, wherein the processor is configured to perform a new task of tissue processing while a sample basket comprising a tissue sample under processing is left inside a container, and wherein the processor is configured to prevent human-induced errors based on the rules stored in the rule database while processing the tissue samples, and wherein the processor is configured to prioritize a plurality of processing tasks to avoid a conflict, and wherein the processor is configured to process emergency samples without any conflict or interference with a processing operation under progress, and wherein the processor is configured to move the robotic arm to automatically choose a similar reagent container when a reagent station defined by a processing program is already engaged with another sample basket, and wherein the processor is configured to halt a tissue processing operation, when the tissue processing operation under progress needs a specific reagent which does not exist in the containers, and wherein the processor is configured to halt a tissue processing operation till the required reagent is available in the containers.

6. The system according to claim 1, wherein the user interface is configured to allow the user to freely design and modify each step of the tissue processing program or operation.

7. The system according to claim 1 further comprises a plurality of rails, a plurality of stepper motors, a plurality of time chains, a plurality of wagons, and a plurality of spools to move the robotic arm in an upward direction and down ward direction along Z-axis and to move the robotic arm in left and right directions along X-axis and Y-axis.

8. The system according to claim 1, further comprises an exhaust facility with a filtration system with to prevent toxic gases emission from the equipment during the tissue processing and slide staining operations.

9. The system according to claim 1, the equipment further comprises standard signs and alarms to provide an alert or notification to the user regarding a plurality of errors and to protect the user from any possible harm.

10. The system according to claim 1, the equipment further comprises a plurality of heating stations to adjust a temperature inside the containers to a preset value, wherein the preset value is set by the user through the user interface.

11. The system according to claim 1, the equipment further comprises:
    a hydraulic door support jack;
    a battery box for supplying electrical power;
    an electronic board box for housing a processor, a memory and a data base;
    a plurality of movement sensors for detecting and controlling a movement of the robotic arm along X-axis, Y-axis, and Z-axis;
    a plurality of cable chains connected to the robotic arm;
    a paraffin temperature control unit for controlling a temperature inside the system;
    a solenoid valve;
    a plurality of legs for supporting the system/chassis;
    a margin;
    a plurality of spring pins for positioning the container and for adjusting a position of the containers; and
    a ventilation fan for exhausting the toxic gases and contaminants.

12. The system according to claim 1, wherein the gripper is designed and configured to grip and hold the one of the sample baskets and one of the lids in the plurality of containers.

13. The system according to claim 1, wherein the user interface is configured to displays choices of menus, buttons, dialogs, and callouts to guide the user to provide inputs during a programming of tissue processing and staining operations.

14. The system according to claim 1, wherein the user interface is configured to provide details related to a resident time or reaction of tissue sample with a reagent in the reaction container, sample basket shaking method and pattern inside the reagent container.

15. The system according to claim 1, wherein the processor is configured to adjust a reaction time and a shaking pattern and duration of a sample basket outside the reagent container to control a reagent carry-over contamination.

16. The system according to claim 1, wherein the containers are designed to prevent an inadvertent opening of the lid during a tissue processing and staining operation.

17. The system according to claim 1, wherein the sample basket is designed to hold the slides in a vertical manner and wherein the slides are designed to hold the tissue samples.

18. The system according to claim 1, wherein the containers are designed and configured to wash the sample baskets with a running water.

19. The system according to claim 1, wherein the preset rules are generated based on inputs received from a plurality of professional pathologists.

* * * * *